United States Patent [19]

Lafon

[11] 4,372,969

[45] Feb. 8, 1983

[54] ADDITION SALTS OF SUBSTITUTED ARALKYLAMINES, THEIR METHOD OF PREPARATION AND THEIR USE AS PHARMACEUTICALS

[75] Inventor: Louis Lafon, Paris, France

[73] Assignee: Societe Anonyme Dite: Laboratoire L. Lafon, Maisons-Alfort, France

[21] Appl. No.: 235,937

[22] Filed: Feb. 19, 1981

Related U.S. Application Data

[63] Continuation of Ser. No. 121,503, Feb. 14, 1980, abandoned, which is a continuation of Ser. No. 967,897, Dec. 11, 1978, abandoned.

[30] Foreign Application Priority Data

Dec. 13, 1977 [GB] United Kingdom ............... 51836/77

[51] Int. Cl.$^3$ .................... A61K 31/36; C07D 317/44; C07C 91/06; A61K 31/135
[52] U.S. Cl. .................................. 424/282; 549/443; 564/363; 424/330
[58] Field of Search ............... 260/340.5 R; 564/363; 424/330, 282; 549/443

[56] References Cited

U.S. PATENT DOCUMENTS

| | | | |
|---|---|---|---|
| 2,493,471 | 1/1950 | Tillitson | 424/330 |
| 2,578,696 | 12/1951 | Gump et al. | 260/340.5 R |
| 2,647,130 | 7/1953 | Kwartler | 260/340.5 R |
| 2,725,399 | 11/1955 | Denton | 424/330 |
| 3,344,188 | 9/1967 | Wollweber et al. | 564/363 |
| 4,012,528 | 3/1977 | Yu-Wen Jen et al. | 260/340.5 R |
| 4,024,274 | 5/1977 | Druckrey et al. | 260/340.5 R |
| 4,147,799 | 4/1979 | Obase et al. | 549/443 |

FOREIGN PATENT DOCUMENTS

| | | | |
|---|---|---|---|
| 2120203 | 4/1971 | Fed. Rep. of Germany. | |
| 1643488 | 6/1971 | Fed. Rep. of Germany. | |
| 2303815 | 8/1974 | Fed. Rep. of Germany. | |
| 1043510 | 9/1966 | United Kingdom | 424/330 |
| 1043519 | 9/1966 | United Kingdom | 564/363 |
| 1135340 | 12/1968 | United Kingdom | 549/443 |
| 1218135 | 1/1971 | United Kingdom. | |

*Primary Examiner*—Ethel G. Love
*Attorney, Agent, or Firm*—Lewis H. Eslinger

[57] ABSTRACT

The present invention relates to addition salts of substituted aralkylamines of formula:

$$A-CH_2-NH-R \qquad (I)$$

[wherein A is a 3,4-methylenedioxyphenyl group or an α-hydroxybenzyl, and R is $CH(CH_3)_2$ or $C(CH_3)_3$]

It relates also to the method for preparing these salts and to their application as pharmaceuticals and in particular as central nervous system antidepressants.

7 Claims, No Drawings

ADDITION SALTS OF SUBSTITUTED ARALKYLAMINES, THEIR METHOD OF PREPARATION AND THEIR USE AS PHARMACEUTICALS

This is a continuation, of application Ser. No. 121,503 filed Feb. 14, 1980, now abandoned, which is a continuation of application Ser. No. 967,897, filed Dec. 11, 1978, now abandoned.

The present invention relates to addition salts of substituted aralkylamines, their method of preparation and their use as pharmaceuticals.

The addition salts according to the invention are acid addition salts obtained from a substituted aralkylamine of formula:

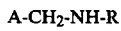  (I)

[wherein A is a 3,4-methylenedioxyphenyl group or an α-hydroxybenzyl, and R is $CH(CH_3)_2$ or $C(CH_3)_3$] and from an organic acid, selected in particular from the group comprising of acetic, propionic, citric, fumaric, maleic, succinic and methanesulphonic acids.

The bases of formula I are substances known *per se*. In particular, N-isopropyl-3,4-methylenedioxybenzylamine (or N-isopropyl-piperonylamine) is known from the *Chemical Abstracts* 50, 4838b and 53, 8073a, the 2-isopropylamino-1-phenyl-1-ethanol being known from the published German Patent Application (OLS) No. 2,052,991, and the 2-tertiobutylamino-1-phenyl-1-ethanol from British Patent No. 1,043,510.

It has just been unexpectedly discovered that the addition salts of the bases of Formula I obtained from organic acids:

(1) are less toxic than the corresponding hydrochlorides, (2) have an anti-depressant action on the central nervous system, and (3) are devoid of any of the bad harmful side-effects on the cardiovascular system presented by Isoproterenol [i.e. 2-isopropyl-amino-1-(3,4-dihydroxyphenyl)-1-ethanol], a reference compound which is similar from the point of view of structure.

The addition salts according to the invention are prepared in accordance with a method known per se. The method recommended consists in reacting the free base with an acid under stoichiometric conditions, in a solvent such as diethyl ether, dimethyl ether, ethanol or methanol.

The invention teaches to use a therapeutic composition suitable for treating disorders of the central nervous system, which has the characteristic of containing, in combination with a physiologically acceptable excipient, at least on addition salt of a substituted aralkylamine with an organic acid, as an anti-depressant agent of the central nervous system. The preferred compounds are, first, the salts of Examples 6 to 11, and second, the salts of Examples 12 to 17, the most interesting ones being those of Examples 8, 10, 13 and 16.

EXAMPLE 1

2-isopropylamino-1-phenyl-1-ethanol acetate

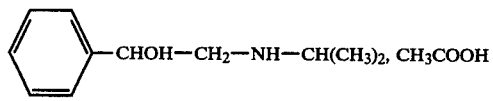

Code No. CRL 40609A (a) 2-isopropylamino-1-phenyl-1-ethanol

A mixture of 120 g (1 mole) styrene oxide and 59 g (1 mole) of isopropylamine are heated under reflux for 5 hours in 400 ml of methanol. The mixture is dry evaporated and the residue is dissolved in 500 ml of water. The desired free base which has precipitated is filtered and the solution is washed with 100 ml of hexane. The base is recrystallized from hexane, and the crystals are filtered and washed with 50 ml hexane and then dried. 89 g (yield=49%) of 2-isopropylamino-1-phenyl-1-ethanol are obtained. M.P. 90° C.

(b) CRL 40609 A 10 g (0.0558 mole) of the free base thus obtained are dissolved in ether. A solution of 3.35 g (0.0558 mole) of acetic acid in 50 ml of ether is then added. The precipitating addition salt is filtered, and then washed in ether and 8.4 g (yield=62%) of CRL 40609 A are obtained. M.P.=85° C.

EXAMPLE 2

2-isopropylamino-1-phenyl-1-ethanol propionate

Code No. CRL 40609B

By proceeding as indicated in Example 1 (b), and replacing the acetic acid with the propionic acid (4.13 g; 0.0558 mole) 8.65 g (yield=61%) of CRL 40609B are obtained. M.P. 88° C.

EXAMPLE 3

2-isopropylamino-1-phenyl-1-ethanol hemifumarate

Code No. CRL 40609C 12 g (0.0670 mole) of 2-isopropylamino-1-phenyl-1-ethanol and 3.886 g (0.0335 mole) of fumaric acid are dissolved in 67 ml of warm anhydrous ethanol. The solution is cooled by an ice bath and the precipitate which has formed is filtered, washed in acetone and dried. 14.1 g (yield=88%) of CRL 40609C are thus obtained. M.P. 156°–158° C.

| Analysis | measured N % = 5.86% |
| --- | --- |
| | theoretical N % = 5.88% |

EXAMPLE 4

2-isopropylamino-1-phenyl-1-ethanol hemisuccinate

Code No. CRL 40609 D

By proceeding as indicated in example 3, but replacing the fumaric acid with succinic acid (3.95 g; 0.0335 mole), 7.8 g (yield=49%) of CRL 40609 D are obtained. M.P.=125° C.

Analysis { measured N %: 5.86%
theoretical N %: 5.88%

EXAMPLE 5

2-isopropylamino-1-phenyl-1-ethanol methanesulphonate

Code No. CRL 40609 E

By proceeding as indicated in Example 1 (b) and replacing the acetic acid by methanesulphonic acid, 13.55 g (yield=88%) of CRL 40609E are obtained. M.P. 102° C.

EXAMPLES 6 to 11

By reacting 2-tertiobutylamino-1-phenyl-1-ethanol (M.P. 89°–90° C.; prepared from 1.5 moles of styrene oxide and 1.84 moles of tertiobutylamine) with organic acids according to the invention, the following are obtained respectively:
acetate (CRL 40 610 A; M.P.=100° C.)
propionate (CRL 40 610 B; M.P.=108° C.),
hemifumarate (CRL 40 610 C; M.P.=150° C.),
hemisuccinate (CRL 40 610 D; M.P.=120° C.),
methanesulphonate (CRL 40 610 E; M.P.=116°–117° C.) and
citrate (CRL 40 610 F; M.P.=116° C.)
of 2-tertiobutylamino-1-phenyl-1-ethanol, the citrate having the structural formula:

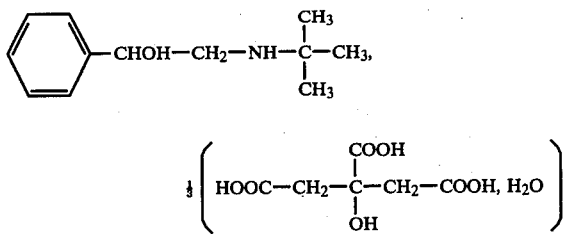

EXAMPLES 12 to 17

By reacting N-isopropyl-piperonylamine with organic acids according to the invention, the following are obtained respectively:
acetate (CRL 40 599 A; P.P.=84° C.),
propionate (CRL 40 599 B; M.P.=76° C.),
fumarate (CRL 40 599 C; M.P.=160° C.),
succinate (CRL 40 599 D; M.P.=125° C.),
methanesulphonate (CRL 40 599 E; M.P. 134° C.), and
citrate (CRL 40 599 F; M.P.=135° C.)
of N-isopropyl-piperonylamine.

Corresponding addition salts are obtained from N-tertiobutyl-piperonylamine and acetic, propionic, fumaric, succinic, methanesulphonic and citric acids.

Pharmacological tests have been carried out and their results are given hereinafter.

(a) Toxicity

The DL-50 was determined in male mice by intraperitoneal route. The following Tables I and II give a comparison of the DL-50 of each organic salt with that of the corresponding hydrochloride.

TABLE I

Toxicity of the 2-tertiobutylamino-1-phenyl-1-ethanol

| Salt | DL-50 of the salt (mg/kg) | DL-50 calculated with respect to the base (mg/kg) |
| --- | --- | --- |
| Acetate (Example 6) | 155 | 118 |
| Propionate (Example 7) | 179 | 129 |
| Hemifumarate (Example 8) | 188 | 145 |
| Hemisuccinate (Example 9) | 157 | 120 |
| Methanesulphonate (Example 10) | 206 | 138 |
| Hydrochloride | 135 | 114 |

TABLE II

Toxicity of the N—isopropyl-piperonylamine salts

| Salt | DL-50 of the salt (mg/kg) | DL-50 calculated with respect to the base (mg/kg) |
| --- | --- | --- |
| Acetate (Example 12) | 190 | 160 |
| Propionate (Example 13) | 235 | 185 |
| Fumarate (Example 14) | 204 | 171 |
| Succinate (Example 15) | 190 | 169 |
| Methanesulphonate (Example 16) | 252 | 184 |
| Citrate (Example 17) | 250 | 177 |
| Hydrochloride | 172 | 135 |

Table I shows that the salts which are the most interesting as regards toxicity are the fumarates and the methanesulphonates for the compounds I wherein A is α-hydroxybenzyl; Table II shows that the most interesting salts are the methanesulphonates and the propionates for compounds I wherein A is 3,4-methylenedioxyphenyl.

(b) Action on the Central Nervous System

When administered by gastric route and by parenteral route the products of Examples 1 to 5 (CRL 40609 A-E) show the same type of activity:
antagonism to reserpinic hypothermia;
antagonism to hypothermia and to a lesser degree to tremblings and to signs of peripheral cholinergic stimulation due to oxotremorine;
antagonism to hypothermia caused by apomorphine; and
reduction of intergroups aggressivity (in the male mouse).

When administered by gastric and by parenteral routes, the products of Examples 6 to 11 (CRL 40 610 A-F) show the same type of activity:
antagonism to hypothermia induced by apomorphine without altering the behaviour of the verticalisation and the stereotypies;
antagonism of hypothermia due to reserpine (2.5 mg/kg intraperitoneal) in doses of 32 to 64 mg/kg in the mouse (at the dose of 128 mg/kg, this effect is no longer clear); and
antagonism to hypothermia induced by oxotremorine without altering the trembling or the peripheral cholinergic symptoms (salivation, lacrymation defecation).

Table III below gives the results obtained with the CRL 40 610 C (Example 8) administered by oral route 30 minutes before administration of apomorphine (batches of six animals per dose; 12 controls).

TABLE III

Antagonism of the product of Example 8 vis-a-vis apomorphine

| Product | Dose (mg/kg) | Temperature (°C) at given time | | | Verticalisation T = +25 mins. | Stereotypies T = +25 mins. |
|---|---|---|---|---|---|---|
| | | T = −30 mins. | T = 0 | T = +30 mins. | | |
| — | (Controls) | 36.1 | 37.0 | 33.1 | 1.75 | 2.75 |
| CRL 40 610 C | 1 | 35.8 | 36.9 | 32.8 | 1.83 | 3.00 |
| | 4 | 36.2 | 37.3 | 34.2 | 1.67 | 2.67 |
| | 16 | 36.1 | 36.9 | 35.3 | 1.67 | 2.50 |
| | 64 | 36.3 | 36.8 | 35.8 | 2.00 | 2.83 |

The products of Examples 12 to 17 (CRL 40 599 A-F) show an antagonism to hypothermia induced by apomorphine, oxotremorine and reserpine. At higher doses, they potentiate the stereotypies of amphetamine and reduce aggressivity.

All these results show that the salts according to the invention are antidepressants of the central nervous system.

These salts can be administered orally to humans as antidepressants, whereas, in general the β-sympathomimetic antagonists which are structurally resembling must be used by parenteral route.

What is claimed is:

1. An acid addition salt of substituted aralkylamine, for use in particular in therapy as antidepressant of the central nervous system, selected from the group consisting of
2-isopropylamino-1-phenyl-1-ethanol methanesulphonate,
2-tertiobutylamino-1-phenyl-1-ethanol hemifumarate,
2-tertiobutylamino-1-phenyl-1-ethanol methanesulphonate,
N-isopropyl-piperonylamine methanesulphonate, and
N-isopropyl-piperonylamine propionate.

2. An acid addition salt of substituted aralkylamine according to claim 1, which is 2-isopropylamino-1-phenyl-1-ethanol methanesulphonate.

3. An acid addition salt of substituted aralkylamine according to claim 1, which is 2-tertiobutylamino-1-phenyl-1-ethanol hemifumarate.

4. An acid addition salt of substituted aralkylamine according to claim 1, which is 2-tertiobutylamino-1-phenyl-1-ethanol methanesulphonate.

5. An acid addition salt of substituted aralkylamine according to claim 1, which is N-isopropylpiperonylamine methanesulphonate.

6. An acid addition salt of substituted aralkylamine according to claim 1, which is N-isopropyl-piperonylamine propionate.

7. A pharmaceutical composition for alleviating depression of the central nervous system comprising an antidepressant effective amount of a component of claim 1.

* * * * *